US 12,318,151 B2

United States Patent
Krimsky

(10) Patent No.: US 12,318,151 B2
(45) Date of Patent: *Jun. 3, 2025

(54) INTEGRATION OF MULTIPLE DATA SOURCES FOR LOCALIZATION AND NAVIGATION

(71) Applicant: Covidien LP, Mansfield, MA (US)

(72) Inventor: William S Krimsky, Forest Hill, MD (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/382,982

(22) Filed: Oct. 23, 2023

(65) Prior Publication Data

US 2024/0050166 A1 Feb. 15, 2024

Related U.S. Application Data

(63) Continuation of application No. 15/895,012, filed on Feb. 13, 2018, now Pat. No. 11,793,579.
(Continued)

(51) Int. Cl.
*A61B 34/20* (2016.01)
*A61B 1/267* (2006.01)
(Continued)

(52) U.S. Cl.
CPC .............. *A61B 34/20* (2016.02); *A61B 5/062* (2013.01); *A61B 5/066* (2013.01); *A61B 6/032* (2013.01);
(Continued)

(58) Field of Classification Search
None
See application file for complete search history.

(56) References Cited

U.S. PATENT DOCUMENTS

| 5,057,494 A | 10/1991 | Sheffield |
| 5,321,113 A | 6/1994 | Cooper et al. |

(Continued)

FOREIGN PATENT DOCUMENTS

| BR | 0013237 A | 7/2003 |
| BR | 0116004 A | 6/2004 |

(Continued)

OTHER PUBLICATIONS

Examination Report issued in corresponding European Appl. No. 18157836.0 dated Dec. 2, 2019 (6 pages).
(Continued)

*Primary Examiner* — Jason M Ip
*Assistant Examiner* — Renee C Langhals
(74) *Attorney, Agent, or Firm* — Weber Rosselli & Cannon LLP

(57) ABSTRACT

Disclosed are systems, devices, and methods for navigating a tool inside a luminal network. An exemplary method includes receiving image data of a patient's chest, identifying the patient's lungs, determining locations of a luminal network in the patient's lungs, identifying a target location in the patient's lungs, generating a pathway to the target location, generating a three-dimensional (3D) model of the patient's lungs, the 3D model showing the luminal network in the patient's lungs and the pathway to the target location, determining a location of a tool based on an electromagnetic (EM) sensor included in the tool as the tool is navigated within the patient's chest, displaying a view of the 3D model showing the determined location of the tool, receiving cone beam computed tomography (CBCT) image data of the patient's chest, updating the 3D model based on the CBCT image data, and displaying a view of the updated 3D model.

16 Claims, 5 Drawing Sheets

Related U.S. Application Data

(60) Provisional application No. 62/462,171, filed on Feb. 22, 2017.

(51) Int. Cl.

| | | |
|---|---|---|
| *A61B 5/06* | (2006.01) | |
| *A61B 5/08* | (2006.01) | |
| *A61B 6/00* | (2024.01) | |
| *A61B 6/03* | (2006.01) | |
| *A61B 6/12* | (2006.01) | |
| *A61B 6/40* | (2024.01) | |
| *A61B 6/46* | (2024.01) | |
| *A61B 6/50* | (2024.01) | |
| *A61B 8/00* | (2006.01) | |
| *A61B 8/08* | (2006.01) | |
| *A61B 17/00* | (2006.01) | |
| *A61B 34/10* | (2016.01) | |
| *A61B 90/00* | (2016.01) | |
| *G06T 7/00* | (2017.01) | |
| *G06T 19/00* | (2011.01) | |
| *G16H 20/40* | (2018.01) | |
| *G16H 30/40* | (2018.01) | |
| *G16H 50/50* | (2018.01) | |

(52) U.S. Cl.
CPC .......... *A61B 6/12* (2013.01); *A61B 6/50* (2013.01); *A61B 6/504* (2013.01); *A61B 34/10* (2016.02); *A61B 90/37* (2016.02); *G06T 7/0012* (2013.01); *G06T 19/003* (2013.01); *G16H 20/40* (2018.01); *G16H 30/40* (2018.01); *G16H 50/50* (2018.01); *A61B 1/2676* (2013.01); *A61B 5/08* (2013.01); *A61B 6/4085* (2013.01); *A61B 6/463* (2013.01); *A61B 6/5217* (2013.01); *A61B 8/0841* (2013.01); *A61B 8/5223* (2013.01); *A61B 2017/00809* (2013.01); *A61B 2034/105* (2016.02); *A61B 2034/107* (2016.02); *A61B 2034/2051* (2016.02); *A61B 2090/3762* (2016.02); *A61B 2090/3764* (2016.02); *G06T 2207/10081* (2013.01); *G06T 2207/30061* (2013.01)

(56) References Cited

U.S. PATENT DOCUMENTS

| | | | |
|---|---|---|---|
| 6,003,517 | A | 12/1999 | Sheffield et al. |
| 6,188,355 | B1 | 2/2001 | Gilboa |
| 6,373,916 | B1 | 4/2002 | Inoue et al. |
| 6,473,634 | B1 | 10/2002 | Barni |
| 7,551,759 | B2 | 6/2009 | Hristov et al. |
| 7,916,918 | B2 | 3/2011 | Suri et al. |
| 8,335,359 | B2 | 12/2012 | Fidrich et al. |
| 8,482,606 | B2 | 7/2013 | Razzaque et al. |
| 8,625,869 | B2 | 1/2014 | Harder et al. |
| 8,706,184 | B2 | 4/2014 | Mohr et al. |
| 8,827,934 | B2 | 9/2014 | Chopra et al. |
| 9,044,254 | B2 | 6/2015 | Ladtkow et al. |
| 9,119,650 | B2 | 9/2015 | Brannan et al. |
| 9,247,992 | B2 | 2/2016 | Ladtkow et al. |
| 9,247,993 | B2 | 2/2016 | Ladtkow et al. |
| 9,259,269 | B2 | 2/2016 | Ladtkow et al. |
| 9,370,398 | B2 | 6/2016 | Ladtkow et al. |
| 9,375,268 | B2 | 6/2016 | Long |
| 9,433,390 | B2 | 9/2016 | Nathaniel et al. |
| 9,833,167 | B2 | 12/2017 | Cohen et al. |
| 9,888,898 | B2 | 2/2018 | Imagawa et al. |
| 9,918,659 | B2 | 3/2018 | Chopra et al. |
| 10,004,558 | B2 | 6/2018 | Long et al. |
| 10,127,629 | B2 | 11/2018 | Razzaque et al. |
| 10,130,316 | B2 | 11/2018 | Funabasama et al. |
| 10,194,897 | B2 | 2/2019 | Cedro et al. |
| 10,373,719 | B2 | 8/2019 | Soper et al. |
| 10,376,178 | B2 | 8/2019 | Chopra |
| 10,405,753 | B2 | 9/2019 | Sorger |
| 10,478,162 | B2 | 11/2019 | Barbagli et al. |
| 10,480,926 | B2 | 11/2019 | Froggatt et al. |
| 10,524,866 | B2 | 1/2020 | Srinivasan et al. |
| 10,555,788 | B2 | 2/2020 | Panescu et al. |
| 10,569,071 | B2 | 2/2020 | Harris et al. |
| 10,603,106 | B2 | 3/2020 | Weide et al. |
| 10,610,306 | B2 | 4/2020 | Chopra |
| 10,638,953 | B2 | 5/2020 | Duindam et al. |
| 10,639,114 | B2 | 5/2020 | Schuh et al. |
| 10,674,970 | B2 | 6/2020 | Averbuch et al. |
| 10,682,070 | B2 | 6/2020 | Duindam |
| 10,702,137 | B2 | 7/2020 | Deyanov |
| 10,706,543 | B2 | 7/2020 | Donhowe et al. |
| 10,709,506 | B2 | 7/2020 | Coste-Maniere et al. |
| 10,772,485 | B2 | 9/2020 | Schlesinger et al. |
| 10,796,432 | B2 | 10/2020 | Mintz et al. |
| 10,823,627 | B2 | 11/2020 | Sanborn et al. |
| 10,827,913 | B2 | 11/2020 | Ummalaneni et al. |
| 10,835,153 | B2 | 11/2020 | Rafii-Tari et al. |
| 10,885,630 | B2 | 1/2021 | Li et al. |
| 10,896,506 | B2 | 1/2021 | Zhao et al. |
| 2002/0147462 | A1 | 10/2002 | Mair et al. |
| 2003/0013972 | A1 | 1/2003 | Makin |
| 2004/0120981 | A1 | 6/2004 | Nathan |
| 2008/0045938 | A1 | 2/2008 | Weide et al. |
| 2009/0088632 | A1* | 4/2009 | Khamene ............... G06T 7/75 600/424 |
| 2010/0310140 | A1 | 12/2010 | Schneider et al. |
| 2011/0085720 | A1 | 4/2011 | Averbuch |
| 2013/0303945 | A1 | 11/2013 | Blumenkranz et al. |
| 2014/0035798 | A1 | 2/2014 | Kawada et al. |
| 2014/0046211 | A1 | 2/2014 | Ladtkow et al. |
| 2014/0270441 | A1 | 9/2014 | Baker et al. |
| 2014/0281961 | A1 | 9/2014 | Baker et al. |
| 2014/0282216 | A1 | 9/2014 | Baker et al. |
| 2014/0343146 | A1 | 11/2014 | Lepine et al. |
| 2014/0343416 | A1* | 11/2014 | Panescu ............. A61N 5/1077 600/431 |
| 2015/0073266 | A1 | 3/2015 | Brannan et al. |
| 2015/0117733 | A1* | 4/2015 | Manjeshwar ......... G06T 11/003 382/131 |
| 2015/0148690 | A1 | 5/2015 | Chopra et al. |
| 2015/0265368 | A1 | 9/2015 | Chopra et al. |
| 2016/0000302 | A1 | 1/2016 | Brown et al. |
| 2016/0000356 | A1 | 1/2016 | Brown et al. |
| 2016/0005193 | A1 | 1/2016 | Markov et al. |
| 2016/0016007 | A1 | 1/2016 | Bharat et al. |
| 2016/0038248 | A1 | 2/2016 | Bharadwaj et al. |
| 2016/0058507 | A1 | 3/2016 | Dickhans et al. |
| 2016/0157939 | A1 | 6/2016 | Larkin et al. |
| 2016/0174873 | A1 | 6/2016 | Greenburg et al. |
| 2016/0183841 | A1 | 6/2016 | Duindam et al. |
| 2016/0192860 | A1 | 7/2016 | Allenby et al. |
| 2016/0287344 | A1 | 10/2016 | Donhowe et al. |
| 2016/0302747 | A1 | 10/2016 | Averbuch |
| 2016/0317224 | A1 | 11/2016 | Girotto et al. |
| 2017/0035380 | A1 | 2/2017 | Barak et al. |
| 2017/0112571 | A1 | 4/2017 | Thiel et al. |
| 2017/0112576 | A1 | 4/2017 | Coste-Maniere et al. |
| 2017/0209071 | A1 | 7/2017 | Zhao et al. |
| 2017/0265952 | A1 | 9/2017 | Donhowe et al. |
| 2017/0311844 | A1 | 11/2017 | Zhao et al. |
| 2017/0319165 | A1 | 11/2017 | Averbuch |
| 2018/0055582 | A1 | 3/2018 | Krimsky et al. |
| 2018/0078318 | A1 | 3/2018 | Barbagli et al. |
| 2018/0144092 | A1 | 5/2018 | Flitsch et al. |
| 2018/0153621 | A1 | 6/2018 | Duindam et al. |
| 2018/0235709 | A1 | 8/2018 | Donhowe et al. |
| 2018/0240237 | A1 | 8/2018 | Donhowe et al. |
| 2018/0256262 | A1 | 9/2018 | Duindam et al. |
| 2018/0263706 | A1 | 9/2018 | Averbuch |
| 2018/0279852 | A1 | 10/2018 | Rafii-Tari et al. |
| 2018/0325419 | A1 | 11/2018 | Zhao et al. |
| 2019/0000559 | A1 | 1/2019 | Berman et al. |
| 2019/0000560 | A1 | 1/2019 | Berman et al. |

(56) References Cited

U.S. PATENT DOCUMENTS

| | | |
|---|---|---|
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0110839 A1 | 4/2019 | Rafii-Tari et al. |
| 2019/0175062 A1 | 6/2019 | Rafii-Tari et al. |
| 2019/0175799 A1 | 6/2019 | Hsu et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0239723 A1 | 8/2019 | Duindam et al. |
| 2019/0239831 A1 | 8/2019 | Chopra |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0269818 A1 | 9/2019 | Dhanaraj et al. |
| 2019/0269819 A1 | 9/2019 | Dhanaraj et al. |
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0054408 A1 | 2/2020 | Schuh et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078023 A1 | 3/2020 | Cedro et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138514 A1 | 5/2020 | Blumenkranz et al. |
| 2020/0138515 A1 | 5/2020 | Wong |
| 2020/0142013 A1 | 5/2020 | Wong |
| 2020/0155116 A1 | 5/2020 | Donhowe et al. |
| 2020/0155232 A1 | 5/2020 | Wong |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188021 A1 | 6/2020 | Wong et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |
| 2020/0383750 A1 | 12/2020 | Kemp et al. |
| 2021/0000524 A1 | 1/2021 | Barry et al. |

FOREIGN PATENT DOCUMENTS

| | | |
|---|---|---|
| BR | 0307259 A | 12/2004 |
| BR | 0412298 A2 | 9/2006 |
| BR | 112018003862 A2 | 10/2018 |
| CN | 1670769 A | 9/2005 |
| CN | 102858229 A | 1/2013 |
| CN | 103269752 A | 8/2013 |
| CN | 106068451 A | 11/2016 |
| CN | 106821498 A | 6/2017 |
| CZ | 1644519 A | 12/2008 |
| CZ | 486540 B1 | 9/2016 |
| CZ | 2709512 B6 | 8/2017 |
| CZ | 2884879 B1 | 1/2020 |
| EP | 1644519 B1 | 12/2008 |
| EP | 2141497 A1 | 1/2010 |
| EP | 3178435 A1 | 6/2017 |
| EP | 3289964 A1 | 3/2018 |
| EP | 3413830 A4 | 9/2019 |
| EP | 3565498 A1 | 11/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| EP | 3749239 A1 | 12/2020 |
| MX | PA03005028 A | 1/2004 |
| MX | PA03000137 A | 9/2004 |
| MX | PA03006874 A | 9/2004 |
| MX | 225663 B | 1/2005 |
| MX | 226292 B | 2/2005 |
| MX | PA03010507 A | 7/2005 |
| MX | PA05011725 A | 5/2006 |
| MX | 06011286 A | 3/2007 |
| MX | 246862 B | 6/2007 |
| MX | 2007006441 A | 8/2007 |
| MX | 265247 B | 3/2009 |
| MX | 284569 B | 3/2011 |
| WO | 0010456 A1 | 3/2000 |
| WO | 0167035 A1 | 9/2001 |
| WO | 2004019799 A2 | 3/2004 |

OTHER PUBLICATIONS

Extended European Search Report for European Patent Application No. 18157836.0, dated Jul. 23, 2018 (14 pages).

Extended European Search Report issued in European Patent Application No. 21203268.4 dated Jan. 24, 2022.

Leira, H. O., Amundsen, T., Tangen, G. A., Bø, L. E., Manstad-Hulaas, F., & Langø, T., "A novel research platform for electromagnetic navigated bronchoscopy using cone beam CT imaging and an animal model.", 2011, Minimally Invasive Therapy & Allied Technologies, 20(1), 30-41. (Year: 2011).

Office Action issued in corresponding Chinese Appl. No. 201810153779.9 dated Jun. 12, 2020, (14 pages) together with English language translation (16 pages).

The Third Office Action issued in Chinese Patent Application No. 201810153779.9 dated Jul. 9, 2021 with Engl. translation.

Yaniv Ziv et al.: "Electromagnetic Tracking in the Clinical Environment", Medical Physics, AIP, Melville, NY, US, vol. 36, No. 3, Feb. 19, 2009, pp. 876-892.

* cited by examiner

INTEGRATION OF MULTIPLE DATA SOURCES FOR LOCALIZATION AND NAVIGATION

CROSS REFERENCE TO RELATED APPLICATION

The present application is a continuation of U.S. patent application Ser. No. 15/895,012 filed Feb. 13, 2018, now allowed, which claims the benefit of and priority to U.S. Provisional Application Ser. No. 62/462,171, filed on Feb. 22, 2017 the entire contents of which are incorporated herein by reference.

BACKGROUND

Technical Field

The present disclosure relates to the capture, analysis, and integration of data from multiple sources into a chest navigation system, and, more specifically, to systems, devices, and methods for using the chest navigation system including integrated data from a plurality of sources.

Description of Related Art

Pulmonary disease may cause one or more portions of a patient's lungs to lose its ability to function normally and thus may need to be treated. Lung treatment procedures may be very complex and would be greatly aided if the surgeon performing the procedure can visualize the way the diseased lung portions are shaped, such as how the different portions of the lungs are developed and/or may have been deformed due to the disease.

Generally, a patient's lungs are divided into 5 lobes: an upper, middle, and lower lobe comprising the right lung, and an upper and lower lobe comprising the left lung. The lungs are surrounded by the pulmonary pleura (or pleural surfaces). The pleura are composed of two serous membranes: the outer parietal pleura line the inner wall of the rib cage, and the inner visceral pleura directly line the surface of the lungs. The lung lobes are formed by recessions in the pleura, also known as fissures. The fissures are double folds of the pleura that section the lungs into the different lobes. Both the right and left lungs also have a central recession called the hilum at the root of the lung where airways, vascular, and lymphatic lumens pass into the lungs.

Systems for displaying images and tracking tools in the patient's lungs generally rely on pre-operative data, such as from computed tomography (CT) scans performed before, sometimes days or weeks in advance, the treatment procedure begins. However, such systems do not account for changes that may have occurred after the CT scan was performed, nor do they account for the changes related to the respiratory cycle compared to the original dataset, which is typically acquired at or close to total lung capacity, as well as changes in lung volume that occur during the procedure. Systems, devices, and methods for improving on the process of identifying and visualizing a patient's lungs, as well as structures located therein, are described below.

SUMMARY

Provided in accordance with the present disclosure is a method of navigating a tool inside a luminal network. According to an aspect of the present disclosure, the method includes receiving image data of a patient's chest, identifying the patient's lungs in the image data, determining locations of a luminal network in the patient's lungs in the image data, identifying a target location in the patient's lungs, generating a pathway to the target location, generating a three-dimensional (3D) model of the patient's lungs based on the image data, the 3D model showing the luminal network in the patient's lungs and the pathway to the target location, determining a location of a tool based on an electromagnetic (EM) sensor included in the tool as the tool is navigated within the patient's chest, displaying a view of the 3D model showing the determined location of the tool, receiving cone beam computed tomography (CBCT) image data of a portion of the patient's chest based on an intra-procedural CBCT scan performed after the tool has at least partially been navigated within the patient's chest, updating at least a portion of the 3D model based on the CBCT image data, and displaying a view of the updated 3D model.

In another aspect of the present disclosure, the method further includes displaying a comparison of the image data of the patient's chest and the CBCT image data.

In yet another aspect of the present disclosure, the method further includes identifying an actual location of the tool based on the CBCT image data, and displaying the view of the updated 3D model includes displaying the actual location of the tool at a given lung volume.

In still another aspect of the present disclosure, the method further includes tracking the location of the tool within the patient's chest as the tool is navigated to the target location.

In a further aspect of the present disclosure, the method further includes identifying an actual position of the target location based on the CBCT image data, wherein displaying the view of the updated 3D model includes displaying the actual position of the target location.

In another aspect of the present disclosure, the method further includes identifying an actual location of the tool based on the CBCT image data, identifying an actual position of the target location based on the CBCT image data, generating an updated pathway between the actual location of the tool and the actual position of the target location, and displaying the updated pathway on the updated 3D model.

In a further aspect of the present disclosure, the method further includes displaying a localized portion of the updated 3D model including the actual location of the tool, the actual position of the target location, and the updated pathway.

In another aspect of the present disclosure, the CBCT image data is acquired during a normal tidal breathing phase of the patient's respiratory cycle.

Provided in accordance with the present disclosure is a non-transitory computer-readable storage medium storing instructions which, when executed by a computer, cause the computer to receive image data of a patient's chest, identify the patient's lungs in the image data, determine locations of a luminal network in the patient's lungs in the image data, identify a target location in the patient's lungs, generate a pathway to the target location, generate a three-dimensional (3D) model of the patient's lungs based on the image data, the 3D model showing the luminal network in the patient's lungs and the pathway to the target location, determine a location of a tool based on an electromagnetic (EM) sensor as the tool is navigated within the patient's chest, cause a display device to display a view of the 3D model showing the determined location of the tool, receive cone beam computed tomography (CBCT) image data of a portion of the patient's chest based on an intra-procedural scan performed after the tool has at least partially been navigated within the patient's chest, update at least a portion of the 3D model based on the CBCT image data, and cause the display device to display a view of the updated 3D model.

In another aspect of the present disclosure, the instructions further cause the computer to cause the display device to display a comparison of the image data of the patient's chest and the CBCT image data.

In yet another aspect of the present disclosure, the instructions further cause the computer to identify an actual location of the tool based on the CBCT image data, and cause the display device to display a view of the updated 3D model that includes the actual location of the tool at a given lung volume.

In still another aspect of the present disclosure, the instructions further cause the computer to cause the display device to iteratively update the displayed location of the tool within the patient's chest as the tool is navigated to the target location.

In a further aspect of the present disclosure, the instructions further cause the computer to identify an actual position of the target location based on the CBCT image data, and cause the display device to display a view of the updated 3D model that includes the actual position of the target location.

In another aspect of the present disclosure, the instructions further cause the computer to identify an actual location of the tool based on the CBCT image data, identify an actual position of the target location based on the CBCT image data, generate an updated pathway between the actual location of the tool and the actual position of the target location, and cause the display device to display the updated pathway on the updated 3D model.

In a further aspect of the present disclosure, the instructions further cause the computer to cause the display device to display a localized portion of the updated 3D model including the actual location of the tool, the actual position of the target location, and the updated pathway.

In another aspect of the present disclosure, the CBCT image data is acquired during a normal tidal breathing phase of the patient's respiratory cycle.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

Figure 1:
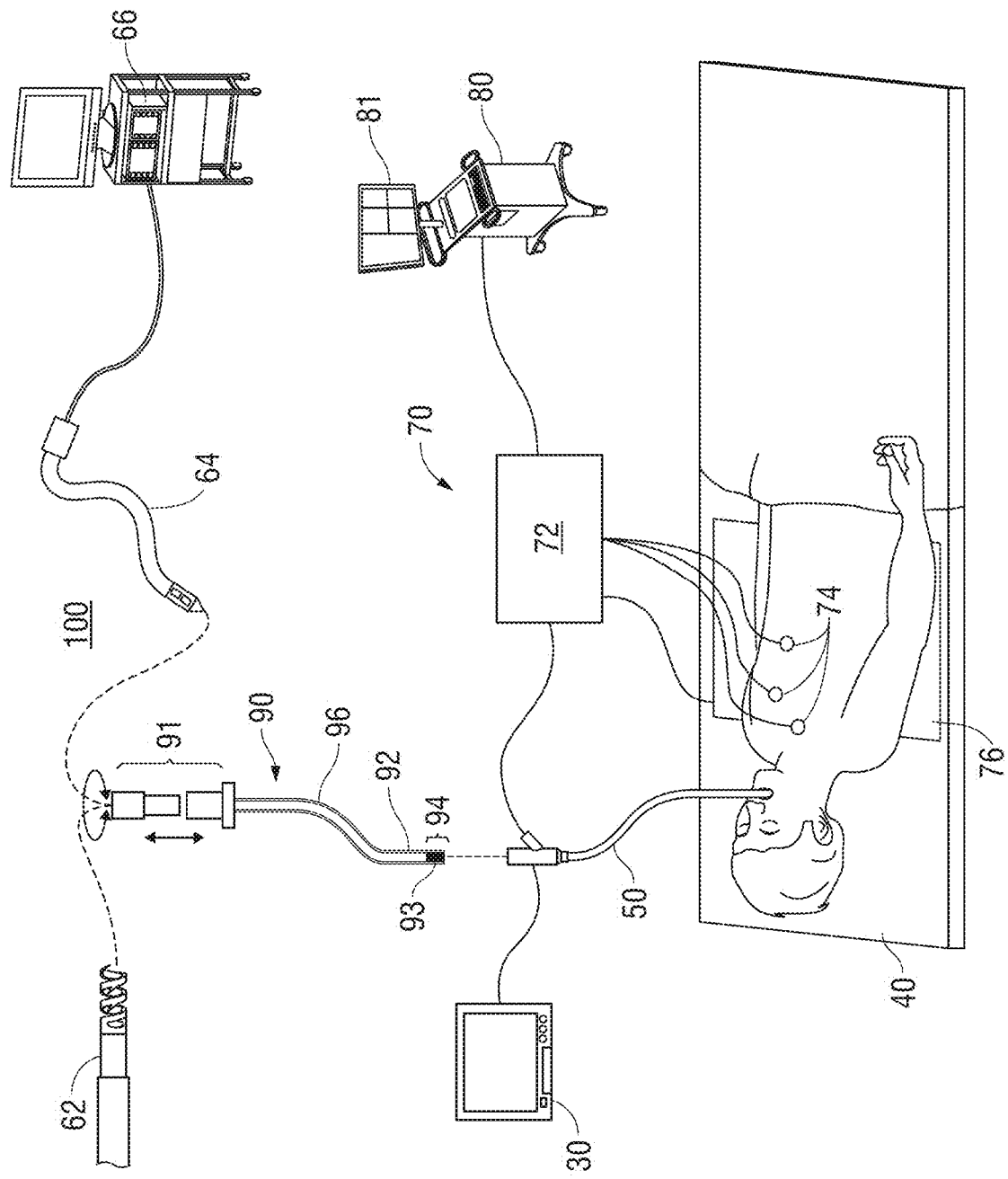
FIG. 1 is a schematic diagram of an endobronchial system for planning and performing diagnostic and treatment procedures in a patient's chest, according to an embodiment of the present disclosure.

The present disclosure is directed to devices, systems, and methods for capturing, analyzing, and integrating data from multiple sources into a chest navigation system. More particularly, the disclosure relates to integrating real-time image data acquired during a procedure with image data acquired prior to the procedure and/or other image data acquired intra-procedurally to update and/or improve localization and visualization of targets and tools within a patient's chest. A preoperative segmental and subsegmental delineation and extrapolation may be performed based on image data of the patient's chest to create a visual representation of a patient's chest, including, for example, airways, pleural surfaces and fissures of the patient's lungs, and/or tumors or other aberrant structures that may be present in the patient's lungs. In addition, various other organs and structures, for example the heart and vascular system, lymph nodes and the lymphatic system, etc., may also be identified in the image data and included in the visual representation of the patient's chest. The delineation may be performed using one or more software applications executing on a computer. The application may, for example, generate a three-dimensional (3D) model or map of the patient's chest based on radiographically obtained images data, such as computed tomography (CT) image data, to use for the visual representation of the patient's chest. The 3D model may show, among other things, the airways, pleural surfaces and fissures, and other structures of the patient's lungs, the heart and/or vascular system, lymph nodes and/or the lymphatic system, and other relevant structures in the patient's chest. The image data may further be processed to identify one or more targets, such as tumors, lesions, or other aberrant structures, in the patient's chest. For example, the application may identify the locations of lumens, such as airways, blood vessels, and/or lymphatic structures from the CT image data, and, based on the locations of the lumens, determine where lung fissures are located and a degree of completeness of the fissures, as well as determine the locations of the pleural surfaces and/or targets. The 3D model and radiographic image data may then be viewed by a clinician and/or surgeon to plan a medical procedure, such as a diagnostic procedure, and/or a treatment procedure such as an ablation procedure or a surgical or interventional procedure. The 3D model and/or procedure plan may further be stored for later viewing during the medical procedure in an operating room or the like.

During the medical procedure, the 3D model may be displayed, as further described below, to assist the clinician in navigating one or more tools to one or more selected targets. At various times during the medical procedure, additional image data may be collected to show a real-time location of the tools and/or the targets in the patient's chest. For example, as a tool approaches a target, or at any other time of the clinician's choosing, a cone beam computed tomography (CBCT) scan, or any other applicable imaging modality, may be performed and the acquired image data processed to identify an actual location of the tool and/or the target in real-time. The 3D model may then be updated based on the image data collected from the CBCT scan, thereby showing the updated location of the tool and/or the target. The image data collected from the CBCT scan may further show, and thus provide a software application the ability to track, the location of the tool during various phases of the patient's respiratory cycle and at various lung capacities. While the initial 3D model may be generated based on image data acquired while the patient was in a particular phase of the respiration cycle, e.g. full breath hold, the patient will be at a different lung volume/capacity during the medical procedure as well as cycling through normal tidal volume breathing during the medical procedure. Thus, acquiring intra-procedural image data at various phases of the patient's respiratory cycle, particularly during normal tidal volume breathing, may provide a clearer and more accurate visualization of the location of the tools and targets inside the patient's chest, as well as the position of the tools relative to the targets. As such, the intra-procedural CBCT scan may be used to confirm placement of the tools at the targets.

The methods, systems, devices, and computer-readable media described herein are useful in various planning and/or navigation contexts for diagnostic and/or treatment procedures performed in the patient's lungs and surrounding tissue in the patient's chest. For example, in an embodiment in which a clinician is performing treatment of an area of the patient's lungs, the methods and systems may provide the clinician with various views of the patient's lungs and the location of the tools and targets therein. Additionally, as will be described in further detail below, the methods and systems may provide the clinician with the ability to update the 3D model at a time of the clinician's choosing, by performing and integrating data from one or more intra-procedural CBCT scans to collect updated location data of the location of the tools and/or targets in the patient's chest. These and other aspects of the present disclosure are detailed hereinbelow.

Methods for planning and performing diagnostic and/or treatment procedures in a patient's chest may be implemented via an electromagnetic navigation (EMN) system. Generally, in an embodiment, the EMN system may be used in planning to reach an area of the patient's lungs by identifying the locations of one or more targets in the patient's lungs, selecting one or more of the targets as a target location, determining a pathway to the target location, navigating a positioning assembly to the target location, and navigating a variety of tools, such as treatment tools, biopsy tools, etc., to the target location. The EMN system may be configured to display various views of the patient's chest, and of the aforementioned 3D model.

With reference to FIG. 1, an EMN system 100 suitable for implementing methods for performing diagnostic and treatment procedures in a patient's chest is provided in accordance with the present disclosure. One such EMN system 100 is the ELECTROMAGNETIC NAVIGATION BRONCHOSCOPY® system currently sold by Covidien LP. As shown in FIG. 1, EMN system 100 is used to perform one or more treatment procedures on a patient supported on an operating table 40. In this regard, EMN system 100 generally includes a bronchoscope 50, monitoring equipment 30, an electromagnetic (EM) tracking system 70, and a computing device 80.

Bronchoscope 50 is configured for insertion through the patient's mouth and/or nose into the patient's airways. Bronchoscope 50 includes a source of illumination and a video imaging system (not explicitly shown) and is coupled to monitoring equipment 30, for example, a video display, for displaying the video images received from the video imaging system of bronchoscope 50. In an embodiment, bronchoscope 50 may operate in conjunction with a catheter guide assembly 90. Catheter guide assembly 90 includes a locatable guide (LG) 92 and an extended working channel (EWC) 96 configured for insertion through a working channel of bronchoscope 50 into the patient's airways (although the catheter guide assembly 90 may alternatively be used without bronchoscope 50). Catheter guide assembly 90 includes a handle 91 connected to EWC 96, and which can be manipulated by rotation and compression to steer LG 92 and EWC 96. EWC 96 is sized for placement into the working channel of bronchoscope 50. In the operation of catheter guide assembly 90, LG 92, including an EM sensor 94, is inserted into EWC 96 and locked into position such that EM sensor 94 extends a desired distance beyond a distal tip 93 of EWC 96. The location of EM sensor 94, and thus distal tip 93 of EWC 96, within an EM field generated by EM field generator 76, can be derived by tracking module 72 and computing device 80. For a more detailed description of catheter guide assembly 90, reference is made to commonly-owned U.S. Pat. No. 9,247,992, entitled "MICROWAVE ABLATION CATHETER AND METHOD OF UTILIZING THE SAME", filed on Mar. 15, 2013, by Ladtkow et al., the entire contents of which are hereby incorporated by reference.

LG 92 and EWC 96 are selectively lockable relative to one another via a locking mechanism 99. A six degrees-of-freedom EM tracking system 70, e.g., similar to those disclosed in U.S. Pat. No. 6,188,355 and published PCT Application Nos. WO 00/10456 and WO 01/67035, entitled "WIRELESS SIX-DEGREE-OF-FREEDOM LOCATOR", filed on Dec. 14, 1998 by Gilboa, the entire contents of each of which is incorporated herein by reference, or any other suitable positioning measuring system, is utilized for performing navigation, although other configurations are also contemplated.

EM tracking system 70 may be configured for use with catheter guide assembly 90 to track a position of EM sensor 94 as it moves in conjunction with EWC 96 through the airways of the patient, as detailed below. In an embodiment, EM tracking system 70 includes a tracking module 72, a plurality of reference sensors 74, and an EM field generator 76. As shown in FIG. 1, EM field generator 76 is positioned beneath the patient. EM field generator 76 and the plurality of reference sensors 74 are interconnected with tracking module 72, which derives the location of each reference sensor 74 in the six degrees of freedom. One or more of reference sensors 74 are attached to the chest of the patient. The six degrees of freedom coordinates of reference sensors 74 are sent as data to computing device 80, which includes application 81, where the data from sensors 74 are used to calculate a patient coordinate frame of reference.

Although EM sensor 94 is described above as being included in LG 92 it is also envisioned that EM sensor 94 may be embedded or incorporated within catheter guide assembly 90 itself, or a tool, such as a biopsy tool 62 and/or an ablation tool 64, where the tool may alternatively be utilized for navigation without need of LG 92 or the necessary tool exchanges that use of LG 92 requires. EM sensor 94 may also be embedded or incorporated within EWC 96, such as at a distal portion of EWC 96, thereby enabling tracking of the distal portion of EWC 96 without the need for a separate LG 92. According to an embodiment, treatment tools 62, 64 are configured to be insertable into catheter guide assembly 90 following navigation to a target location and removal of LG 92. Biopsy tool 62 may be used to collect one or more tissue sample from the target location, and in an embodiment, is further configured for use in conjunction with tracking system 70 to facilitate navigation of biopsy tool 62 to the target location, and tracking of a location of biopsy tool 62 as it is manipulated relative to the target location to obtain the tissue sample. Ablation tool 64 is configured to be operated with a generator 66, such as a radio frequency generator or a microwave generator, and may include any of a variety of ablation tools and/or catheters, examples of which are more fully described in U.S. Pat. Nos. 9,259,269; 9,247,993; 9,044,254; and 9,370, 398, and U.S. Patent Application Publication No. 2014/0046211, all entitled "MICROWAVE ABLATION CATH- ETER AND METHOD OF USING THE SAME", filed on Mar. 15, 2013, by Ladtkow et al., the entire contents of each of which is incorporated herein by reference. Though shown as a biopsy tool and microwave ablation tool in FIG. 1, those of skill in the art will recognize that other tools including for example RF ablation tools, brachytherapy tools, and others may be similarly deployed and tracked without departing from the scope of the present disclosure.

Computing device 80 includes software and/or hardware, such as an application 81, used to facilitate the various phases of an EMN procedure, including generating the 3D model, identifying a target location, planning a pathway to the target location, registering the 3D model with the patient's actual airways, and navigating to the target location. For example, computing device 80 utilizes data acquired from a CT scan, CBCT scan, magnetic resonance imaging (Mill) scan, positron emission tomography (PET) scan, and/or any other suitable imaging modality to generate and display the 3D model of the patient's chest, to enable identification of a target location on the 3D model (automatically, semi-automatically or manually), and allow for the determination and selection of a pathway through the patient's airways to the target location. While the CT scan image data may have gaps, omissions, and/or other imperfections included in the image data, the 3D model is a smooth representation of the patient's airways, with any such gaps, omissions, and/or imperfections in the CT scan image data filled in or corrected. The 3D model may be presented on a display monitor associated with computing device 80, or in any other suitable fashion. An example of the planning software described herein can be found in U.S. Patent Publication Nos. 2014/0281961, 2014/0270441, and 2014/0282216, filed by Baker et al. on Mar. 15, 2013, and entitled "PATHWAY PLANNING SYSTEM AND METHOD", the contents of all of which are incorporated herein by reference. Further examples of the planning software can be found in commonly assigned U.S. Patent Publication No. 2016/0000302, entitled "SYSTEM AND METHOD FOR NAVIGATING WITHIN THE LUNG", filed on Jun. 29, 2015, by Brown et al., the contents of which are incorporated herein by reference.

Using computing device 80, various views of the 3D model may be displayed to and manipulated by a clinician to facilitate identification of a target location. As noted above, the target location may be a surgical site where treatment is to be performed, and/or a portion of, entire lobe, or multiple lobes of the patient's lungs requiring evaluation and treatment. The 3D model may include, among other things, a model airway tree corresponding to the actual airways of the patient's lungs, and show the various passages, branches, and bifurcations of the patient's actual airway tree. Additionally, the 3D model may include lesions, markers, blood vessels and vascular structures, lymphatic vessels and structures, organs, other physiological structures, and/or a 3D rendering of the pleural surfaces and fissures of the patient's lungs. Some or all of the aforementioned elements may be selectively displayed, such that the clinician may choose which elements should be displayed when viewing the 3D model.

During a treatment procedure, EM sensor 94, in conjunction with tracking system 70, enables tracking of EM sensor 94 (and thus distal tip 93 of EWC 96 or tools 62, 64) as EM sensor 94 is advanced through the patient's airways following the pathway planned during the planning phase. As an initial step of the procedure, the 3D model is registered with the patient's actual airways. One potential method of registration, hereinafter referred to as the "lung survey method," involves navigating LG 92 into each lobe of the patient's lungs to at least the second bifurcation of the airways of that lobe. The position of LG 92 is tracked during this registration phase, and the 3D model is iteratively updated based on the tracked position of the locatable guide within the actual airways of the patient's lungs. This registration process is described in commonly-owned U.S. Patent Application Publication No. 2011/0085720, entitled "AUTOMATIC REGISTRATION TECHNIQUE," filed on May 14, 2010, by Barak et al., and U.S. Patent Publication No. 2016/0000356, entitled "REAL-TIME AUTOMATIC REGISTRATION FEEDBACK", filed on Jul. 2, 2015, by Brown et al., the contents of each of which are incorporated herein by reference. While the registration process focuses on aligning the patient's actual airways with the airways of the 3D model, registration also ensures that the position of vascular structures, pleural surfaces, and fissures of the lungs are accurately determined.

At various times during the procedure, the clinician may import additional image data and/or cause additional scans to be performed on the patient. As noted above, these additional scans may be CBCT scans, but those skilled in the art will recognize that other imaging modalities, acoustic approaches as well as predictive models may also be used. For example, ultrasound imaging, C-arm x-ray imaging, fluoroscopic imaging, etc. may also be used without departing from the scope of the present disclosure. The additional scans may be directed at a particular location in the patient's body for which the clinician wants real-time image data regarding the position of EM sensor 94 (representing the location of LG 92 and/or tool 62, 64) and/or target location within the patient's body. Application 81 may receive the image data acquired by the additional scan and process the image data to identify the position of EM sensor 94 and/or the target location within the patient's body. Application 81 may then update and/or enhance the 3D model based on the additional image data. For example, the additional image data may provide a clearer image of the particular part of the patient's body that was imaged by the additional scan than by the original scan, and application 81 may update and/or enhance a portion of the 3D model based on the additional image data. Application 81 may then show a real-time position of EM sensor 94 relative to the target location, and may update the displayed position of EM sensor 94 on the 3D model if the additional image data indicates that the position displayed based on the original image data is incorrect.

Figure 2:
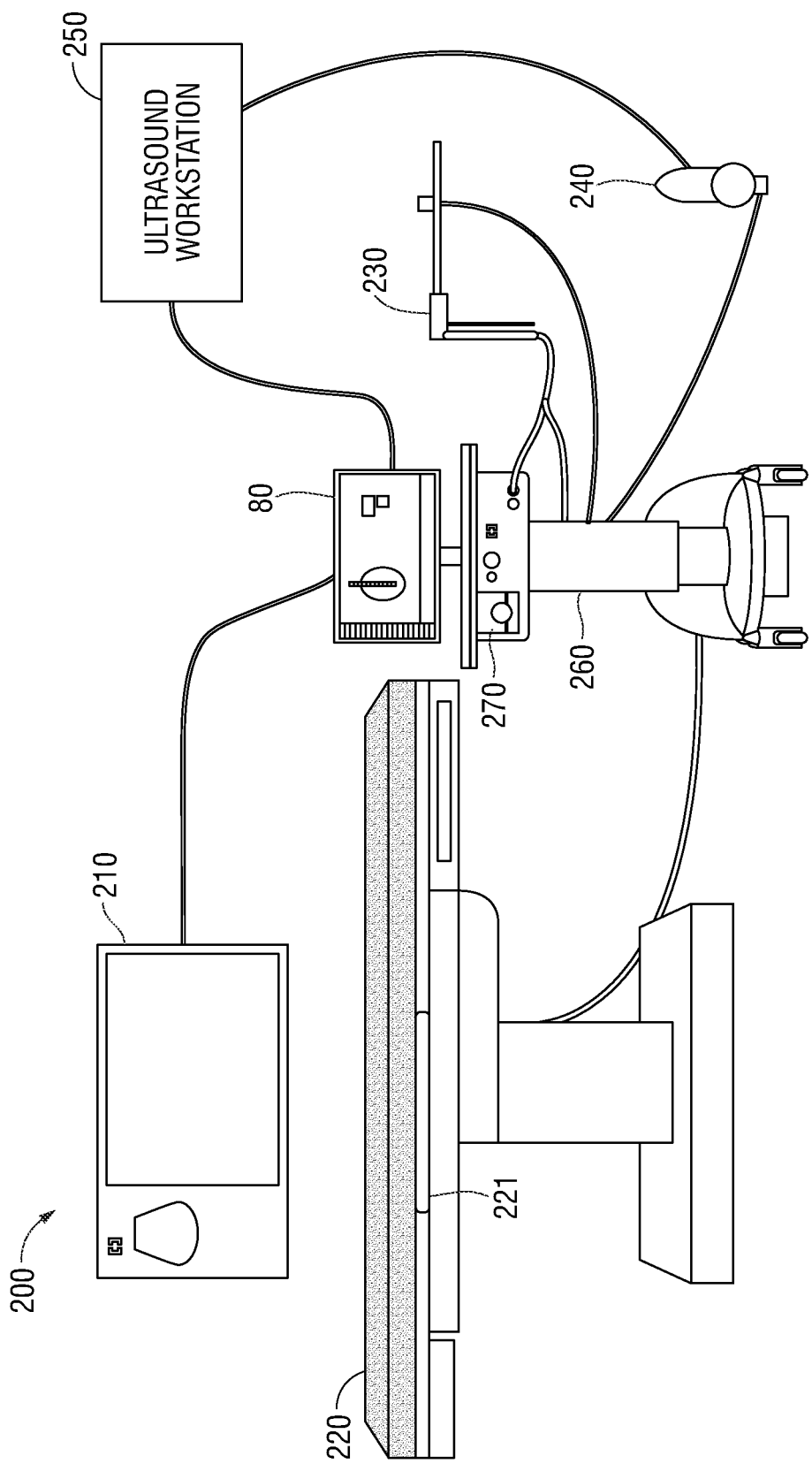
FIG. 2 is a schematic diagram of a percutaneous system for planning and performing diagnostic and treatment procedures in a patient's chest, according to an embodiment of the present disclosure.

Turning now to FIG. 2, there is shown a percutaneous system 200 suitable for implementing methods for performing diagnostic and/or treatment procedures in a patient's chest is provided in accordance with the present disclosure. System 200 includes a display 210, a table 220 including an electromagnetic (EM) field generator 221, a tool 230, an ultrasound sensor 240 connected to an ultrasound workstation 250, a peristaltic pump 260, and a computing device 80 attached to or in operable communication with a microwave generator 270. Computing device 80 may be similar to the computing device 80 described above with reference to FIG. 1. In addition, computing device 80 may be configured to control microwave generator 270, peristaltic pump 260, a power supply (not shown), and/or any other accessories and peripheral devices relating to, or forming part of, system 200. Display 210 is configured to output instructions, images, and messages relating to the performance of the medical procedure.

Table 220 may be, for example, an operating table or other table suitable for use during a medical procedure, which includes EM field generator 221. EM field generator 221 is used to generate an EM field during the medical procedure and forms part of an EM tracking system that is used to track the positions of tools within the patient's chest. EM field generator 221 may include various components, such as a specially designed pad to be placed under, or integrated into, an operating table or patient bed. An example of such an EM tracking system is the AURORA™ system sold by Northern Digital Inc.

Tool 230 is a medical instrument for percutaneously accessing and performing diagnostic and/or treatment procedures at a target location. For example, tool 230 may be an ablation probe having a microwave ablation antenna that is used to ablate tissue. Alternatively, tool 230 may be a cryo-ablation or radiofrequency (RF) ablation probe used to ablate tissue. In some embodiments, tool 230 may include an optical instrument, such as an infrared imaging device, thermal imaging device, a confocal imaging device, an optical coherence tomography (OCT) imaging device, etc. Tool 230 may further include, or have attached to it, various sensors, including a radionuclide detector, a temperature sensor, an optical sensor, and/or an EM sensor enabling the EM tracking system to track the location, position, and orientation (also known as the "pose") of tool 230 inside the patient's chest. Microwave generator 270 may be configured to output microwave energy to tool 230. Peristaltic pump 260 may be configured to pump fluid through tool 230 to cool tool 230. While the present disclosure describes the use of system 200 in a surgical environment, it is also envisioned that some or all of the components of system 200 may be used in alternative settings, for example, an imaging laboratory and/or an office setting.

In addition to the EM tracking system, the above-described instruments may also be visualized by using ultrasound imaging. Ultrasound sensor 240, such as an ultrasound wand, may be used to image one or more portions of the patient's chest during the medical procedure to visualize the location of the instruments, such as tool 230, inside the patient's chest. Ultrasound sensor 240 may have an EM tracking sensor embedded within or attached to the ultrasound wand, for example, a clip-on sensor or a sticker sensor. Ultrasound sensor 240 may be positioned in relation to tool 230 such that tool 230 is at an angle to the ultrasound image plane, thereby enabling the clinician to visualize the spatial relationship of tool 230 with the ultrasound image plane and with objects being imaged. Further, the EM tracking system may also track the location of ultrasound sensor 240. In some embodiments, one or more ultrasound sensors 240 may be placed inside the patient's body. The EM tracking system may then track the location of such ultrasound sensors 240 and tool 230 inside the patient's body. Ultrasound workstation 250 may be used to configure, operate, and/or view images captured by ultrasound sensor 240. Likewise, computing device 80 may be used to configure, operate, and/or view images captured by ultrasound sensor 240, either directly or relayed via ultrasound workstation 250.

Various other instruments or tools, such as LIGASURE™ devices, surgical staplers, etc., may also be used during the performance of the medical procedure. In embodiments where tool 230 is a microwave ablation probe, the microwave ablation probe is used to ablate a lesion or tumor (hereinafter referred to as a "target") by using microwave energy to heat tissue in order to denature or kill cancerous cells. The construction and use of a system including such an ablation probe is more fully described in co-pending U.S. Patent Publication No. 2016/0058507, entitled MICROWAVE ABLATION SYSTEM, filed on Aug. 26, 2014, by Dickhans, U.S. Pat. No. 9,247,992, entitled MICROWAVE ABLATION CATHETER AND METHOD OF UTILIZING THE SAME, filed on Mar. 15, 2013, by Latkow et al., and U.S. Pat. No. 9,119,650, entitled MICROWAVE ENERGY-DELIVERY DEVICE AND SYSTEM, filed on Mar. 15, 2013, by Brannan et al., the entire contents of each of which are hereby incorporated by reference.

As noted above, the location of tool 230 within the patient's chest may be tracked during the medical procedure. An example method of tracking the location of tool 230 is by using the EM tracking system, which tracks the location of tool 230 by tracking sensors attached to or incorporated in tool 230. Various types of sensors may be used, such as a printed sensor, the construction and use of which is more fully described in co-pending U.S. Patent Publication No. US 2016/0174873 14/919,950, entitled "MEDICAL INSTRUMENT WITH SENSOR FOR USE IN A SYSTEM AND METHOD FOR ELECTROMAGNETIC NAVIGATION", filed Oct. 22, 2015, by Greenburg et al., the entire contents of which are incorporated herein by reference. A percutaneous treatment system similar to the above-described system 200 is further described in co-pending U.S. Patent Application Publication No. 2016/0317224, entitled "MICROWAVE ABLATION PLANNING AND PROCEDURE SYSTEMS", filed on Apr. 15, 2016, by Girotto et al., the entire contents of which are incorporated herein by reference.

While the above-described system 200 uses a microwave generator 270 to provide microwave energy to tool 230, those skilled in the art will appreciate that various other types of generators and tools may be used without departing from the scope of the present disclosure. For example, radio frequency (RF) ablation tools receiving RF energy from RF generators may be substituted for the microwave generators and ablation tools described above.

Figure 3A:
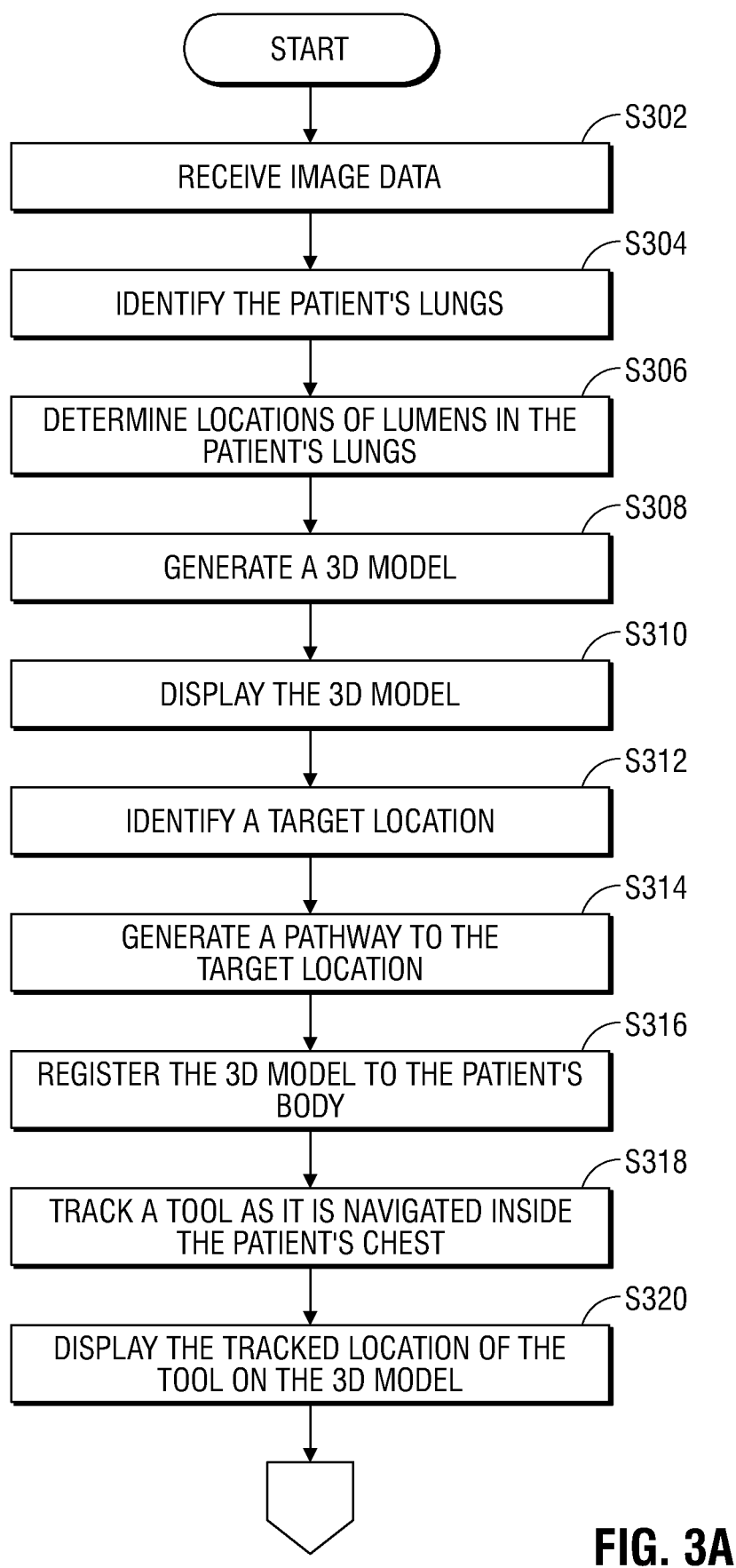
FIGS. 3A and 3B show a flowchart of an example method for planning and performing diagnosis and treatment procedures in a patient's chest, according to an embodiment of the present disclosure.
Figure 3B:
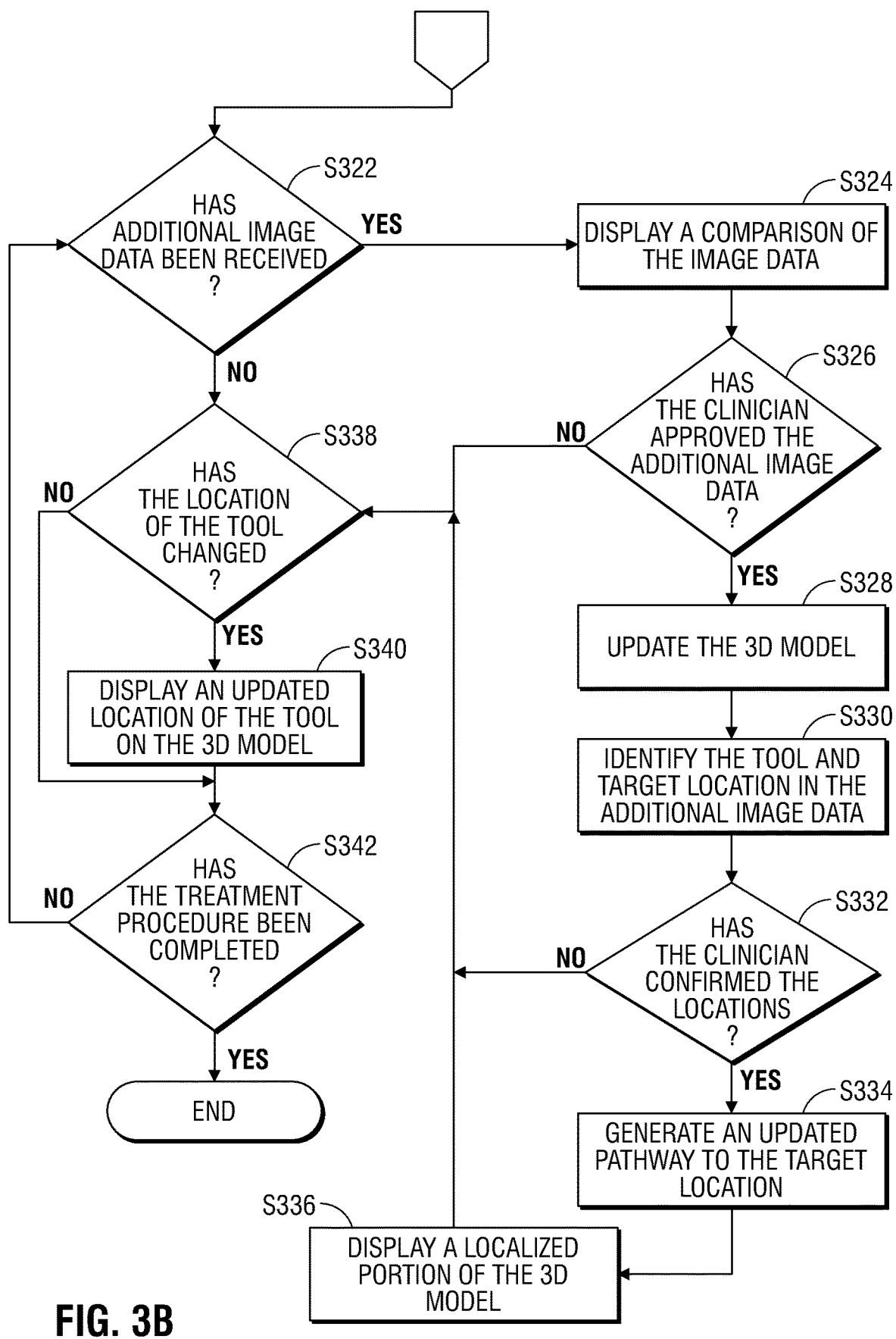

Turning now to FIG. 3, there is shown a flowchart of an exemplary method of performing diagnostic and treatment procedures in a patient's chest, in accordance with an embodiment of the present disclosure. While the below described steps use endobronchial system 100 of FIG. 1 as an example, those skilled in the art will appreciate that percutaneous system 200 of FIG. 2 may be substituted and the below-described steps adapted for a percutaneous procedure without departing from the scope of the present disclosure. Starting at step S302, computing device 80 receives image data of the patient's chest. The image data may be collected by one or more of various imaging modalities, including computed tomography (CT) scans, cone beam computed tomography (CBCT) scans, magnetic resonance imaging (MRI) scans, positron emission tomography (PET) scans, ultrasound scans, X-ray scans, and/or any other relevant imaging modality known to those skilled in the art. In some embodiments, image data from multiple pre-procedural scans may be used in combination. In other embodiments, only image data from a most recent scan may be used. The pre-procedural scans may be performed in advance of the procedure, such as days and/or weeks prior to the procedure, and/or may be performed at the onset of the procedure after the patient has been positioned for the procedure. The image data may be received in, or converted to, a uniform data format, such as the digital imaging and communications in medicine (DICOM) standard.

Next, at step S304, application 81 processes the received image data to identify one or more of the patient's organs in the image data. For example, application 81 may identify the patient's lungs in the image data. The image processing may include automatic and/or user-assisted image analysis to identify the patient's lungs in the image data. Various image processing methods may be used, including region growing techniques, as described in co-pending U.S. Patent Publication No. 2016/0038248, entitled "TREATMENT PROCEDURE PLANNING SYSTEM AND METHOD", filed on Aug. 10, 2015, by Bharadwaj et al., and co-pending U.S. Patent Publication No. 2016/0005193, entitled "SYSTEM AND METHOD FOR SEGMENTATION OF LUNG", filed on Jun. 30, 2015, by Markov et al., the contents of each of which are incorporated herein by reference.

Thereafter, at step S306, application 81 determines the locations of lumens and/or other critical structures in the patient's lungs. The lumens may include airways of the patient's bronchial tree, arteries and veins of the patient's vascular tree, and/or lymphatic lumens and nodes of the patient's lymphatic tree. A healthy lung will typically have separate branches of each of the bronchial, vascular, and lymphatic trees in each lung lobe. However, a diseased or malformed lobe may have lumens from the branches of one or more of these trees fused with lumens from the branches in an adjacent lobe. In such an instance, treating, such as by resection, all or portions of multiple fused lung lobes may be necessary.

Next, at step S308, application 81 generates a three-dimensional (3D) model of the patient's chest. The 3D model includes graphical representations of the patient's lungs, showing the locations of the lumens of the bronchial, vascular, and lymphatic trees, as well as the pleural surfaces and fissures of the patient's lungs, and/or tumors or other aberrant structures that may be present in the patient's lungs. The model may further indicate where incomplete fissures exist and where lumens from adjacent lobes have fused together.

At step S310, the 3D model and the image data are displayed to the clinician, for example, by using a display device such as display 406 of FIG. 4, described below. The clinician may examine various views of the 3D model and the image data and determine which areas of the patient's lungs should be treated. The clinician may further examine the locations and level of completeness of the fissures of the patient's lungs to determine the complexity and scope of the procedure required to treat the diseased areas of the patient's lungs. The clinician may also select one or more target locations by viewing the image data and/or the 3D model at step S312. For example, by using display device 406 and input device 410 of computing device 80 (described in FIG. 4 below), the clinician may view the image data and/or 3D model and may identify and select one or more target locations. The clinician may select and/or mark various areas of the image data to identify those areas as areas that may require diagnosis and/or treatment. The areas may be one or more entire lobes of the patient's lungs, or one or more portions of a single lobe of the patient's lungs, or an identified tumor, lesion or abnormal area within the chest. Thereafter, application 81 may identify and mark a location in the 3D model that corresponds to the location marked by the clinician. Alternatively, or in addition, application 81 may automatically select one or more target locations for diagnosis and/or treatment, for example, by performing image processing and analysis.

Thereafter, at step S314, application 81 may automatically or with input from the clinician, generate a procedure plan, as described further in U.S. Patent Publication No. 2016/0038248, noted above. The procedure plan may include a pathway to the one or more target locations. In the case of an endobronchial procedure, such as by using system 100 of FIG. 1, the pathway may start at the patient's trachea and proceed via the airways and surrounding parenchyma of the patient's lungs to the one or more targets locations. Alternatively, in the case of a percutaneous procedure, such as by using system 200 of FIG. 2, the pathway may start at a point on the patient's skin and proceed to at least one of the target locations through the intervening tissue. Further information regarding the generation of a pathway to the target locations can be found in commonly-owned co-pending U.S. patent application Ser. No. 15/253,084, entitled PATHWAY PLANNING FOR USE WITH A NAVIGATION PLANNING AND PROCEDURE SYSTEM, filed on Aug. 31, 2016, by William S. Krimsky, the entire contents of which are incorporated herein by reference. As will be appreciated by those skilled in the art, consistent with the current iLogic™ planning system described in U.S. Patent Publication No. 2016/0038248, this procedure plan generation may occur prior to the generating of the 3D model by simply viewing the image data, without departing from the scope of the present disclosure.

Following creation of the procedure plan, the 3D model may be registered with the patient's body at step S316, as described above. Thereafter, during the medical procedure at step S318, application 81, via EM tracking system 70, tracks the location of EM sensor 94 as a tool, such as LG 92 or tools 62, 64, is navigated about the patient's airways. For example, application 81 receives EM tracking data from EM tracking system 70 regarding the position of EM sensor 94 within the EM field generated by EM field generator 76 and processes the EM tracking data to determine the location of EM sensor 94 within the patient's airways. Application 81 then displays the tracked location of EM sensor 94 on the 3D model at step S320, thereby providing an indication of the location of the tool inside the patient's chest.

At step S322, application 81 determines whether additional image data has been received. As noted above, the clinician, at various times during the medical procedure, may perform additional scans of the patient's body or import other image data. For example, after navigating the tool about the patient's airways for either a predetermined distance, or at a point selected by the clinician, the clinician may perform a CBCT scan of the patient's body, such as directed at the location where the tool is located and/or the location where the target location is located, to acquire additional image data. Because the additional image data is acquired during the medical procedure, the additional image data is real-time image data, showing an actual position of LG 92 and/or tools 62, 64, within the patient's chest. Likewise, the additional image data can show the actual position of the target location. Due to movement of the airways and surrounding parenchyma (as well as other structures in the patient's lungs) occurring due to the patient's respiratory cycle, the 3D model, which is generated based on image data acquired pre-procedure, may be out of synchronization with the actual position of the airways and other structures in the patient's lungs during some phases of the patient's respiratory cycle and at different lung volumes. Such movement may be accounted and/or compensated for by obtaining real-time image data, as described herein.

As noted hereinbelow, steps S324-S336 describe image processing that may be performed by application 81 at various times during the procedure after additional CBCT image data is received. As depicted and described herein, the image processing of steps S324-S336 is performed during a pause in the navigation phase of the procedure that started at step S316 above, and continues on at step S338 below. During this pause in the navigation phase, LG 92 and/or tools 62, 64 may briefly remain in a fixed position. However, those skilled in the art will appreciate that the image processing of steps S324-S336 may also be performed concurrently with the navigation phase of the treatment procedure, and thus LG 92 and/or tools 62,64 need not remain in a fixed position.

Thus, if additional image data has been received, application 81, at step S324, displays a comparison of the additional image data, the original image data received at step S302, the 3D model, and/or the current position of EM sensor 94. For example, application 81 may process the additional image data similar to the above-described processing of the original image data and display the additional image data and the original image data side-by-side indicating the differences. In some embodiments, application 81 may generate a partial 3D model based on the additional image data and display such a partial 3D model as a comparison and/or an overlay onto the 3D model generated at step S308. The application may then await input from the clinician to approve usage of the additional image data at step S326. If the clinician approves the additional image data, processing proceeds to step S328. Alternatively, if the clinician does not approve the additional image data, processing skips to step S338.

After the clinician approves usage of the additional image data, the additional image data is registered to the 3D model. For example, data obtained during the registration process at step S316 may be fitted and/or aligned with the additional image data to register the additional image data to the 3D model. Alternatively, or in addition, the additional image data and the original image data received at step S302 may be registered and/or aligned based on landmarks and/or fiducial markers identified in the additional and original image data. Application 81 can automatically register the additional image data to the patient's body without the clinician having to repeat the lung survey registration method described above, because the additional image data is acquired intra-procedurally and the patient remains in substantially the same position while the additional image data is acquired as the patient is during the navigation phase of the procedure. Thus, the location of the central airways do not vary significantly after the 3D model is registered to the patient's airways. Additionally, because the target location was identified and/or selected at step S312 based on the 3D model, the registration of the 3D model to the patient's airways performed at step S316 would also align the target location's position in the 3D model with the patient's body based on the registration. Thus, when application 81 registers the additional image data to the 3D model, and application 81 determines that the tracked location of EM sensor 94 relative to the position of the target location in the 3D model is different from the location of LG 92 and/or tools 62, 64 relative to the target location in the additional image data, application 81 may identify one or more portions of the 3D model which should be updated based on the additional image data.

Application 81 may further store reference data regarding the difference in position, and thus the movement, of the target location, LG 92, and/or tools 62, 64 between the original image data and/or 3D model, which is acquired and/or generated during full breath hold, and the additional image data, which is acquired intra-procedurally at various stages of the patient's respiratory cycle. This reference data may be entered into a database and compared with reference data stored during other procedures involving the same patient and/or other patients undergoing similar or related procedures to generate a predictive model of the relative movement of organs and other structures in a patient's chest during the respiratory cycle. After enough data has been assembled for such a predictive model to be generated, application 81 may further include data from the predictive model in the comparison displayed at step S324. In some embodiments, application 81 may further continually update the displayed 3D model during a procedure based on the predicted movement of organs and structures in the patient's chest during the patient's respiratory cycle, thus creating a "breathing 3D model" which reflects the current phase of the patient's respiratory cycle.

At step S328, application 81 updates one or more portions of the 3D model based on the additional image data and/or the partial 3D model. For example, due to the scale and quality of the imaging, the original image data received at step S302 may not include sufficient detail and/or clarity about the airways and other structures at the outer reaches of the airway and/or vascular trees, and thus localized imaging, such as the CBCT imaging described herein, may provide improved detail and/or clarity regarding the outer edges of the airway tree. Thus, application 81 may enhance and/or update one or more portions of the 3D model based on the additional image data. Application 81 may also update the one or more portions of the 3D model which were identified as requiring updating based on differences in the position of EM sensor 94 and/or the target location between the 3D model and the additional image data, as described above.

Thereafter, at step S330, application 81 may process the additional image data to identify a real-time/actual position of the target location and LG 92 and/or tool 62, 64 in the additional image data. While depicted and described as performed after updating the 3D model, the identification of the target location and LG 92 and/or tool 62, 64 in the additional image data may occur at any point after application 81 receives the additional image data. For example, identification of the target location and LG 92 and/or tool 62, 64 may occur as part of the processing of the additional image data performed at step S324. Application 81 may also process the additional image data to determine the locations of lumens and other structures in the patient's lungs, as described above at step S306. After identifying the target location and LG 92 and/or tool 62, 64, application 81 may display an indicator of the identified location of LG 92 and/or tool 62, 64 and the target location on the 3D model. Application 81 may further display an overlay showing the movement of the target location identified at step S312 and the position of the target location identified here at step S330.

Application 82 may then await input from the clinician confirming the identified locations. If the clinician approves the identified location of LG 92 and/or tool 62, 64 and the target location, application 81 updates the displayed location of the indicator representing the position of EM sensor 94 and the target location on the 3D model to the identified locations of LG 92 and/or tool 62, 64 and the target location, and processing proceeds to step S334. Alternatively, if the clinician does not approve the identified locations, processing skips to step S338.

At step S334, application 81 generates an updated pathway from the updated location of the indicator representing the position of EM sensor 94 on the 3D model to the updated location of the target location. In some embodiments, application 81 may further generate and display a new pathway via the patient's airways to the target location, or a trajectory through the parenchyma outside the airways to the target location.

Thereafter, at step S336, application 81 may display a localized portion of the 3D model. For example, the localized portion of the 3D model may be a portion of the 3D model showing the updated pathway to the target location. That is, the localized portion of the 3D model may not include the entire airway tree but rather only include the airway in which LG 92 and/or tool 62, 64 was determined to be located at step S330, and any airways branching off from such airway along the pathway to the target location. In another embodiment, the partial 3D model generated after step S326 (described above) may be used as the localized 3D model, thus reducing the processing demand on computing device 80.

At step S338, application 81 determines whether the tracked location of EM sensor 94, and thus LG 92 and/or tool 62, 64, has changed. If the tracked location of EM sensor 94 has changed, application 81 displays an updated location of EM sensor 94 on the 3D model at step S340. For example, application 81 may iteratively update the displayed location of EM sensor 94 on the 3D model as LG 92 and/or tool 62, 64 is navigated about the patient's chest.

Thereafter, of if the location EM sensor 94 has not changed, processing proceeds to step S342, where application 81 determines if the medical procedure has been completed. If the medical procedure has not been completed, processing returns to step S322, where application 81 again determines if additional image data has been received. Alternatively, if application 81 determines that the medical procedure has been completed, processing ends.

Additional benefits of the above-described systems, devices, and methods include that the clinician may perform additional scans at various times during the medical procedure to more accurately determine the location of the tool in the patient's airways, as well as confirm the position of the target location based on image data that is focused on a particular part of the patient's body. The clinician may further perform additional scans when the tool approaches the target location to confirm placement of the tool at the target location. Based on the additional scans, an updated location of the tool in relation to the target location and based on the current phase of the patient's respiratory cycle may be determined. Thus, following the additional scans, the tool, e.g. a biopsy tool 62, may be advanced directly to the target location, whether inside or outside the patient's airways, because the actual location of the tool and the target location, as well as the position of the tool relative to the target location is known and can be tracked in real-time.

Figure 4:
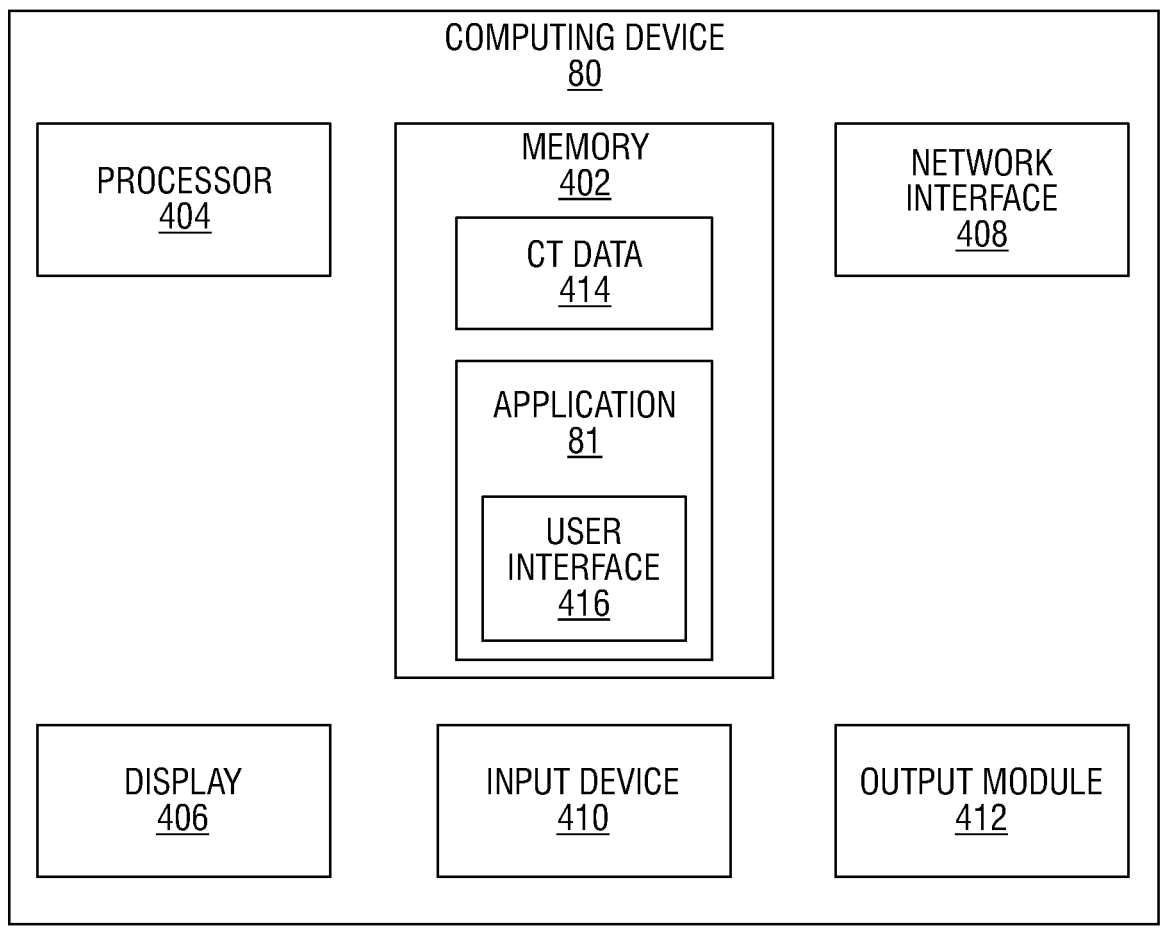
FIG. 4 is a block diagram of an example computing device forming part of the system of FIG. 1, according to an embodiment of the present disclosure.

Turning now to FIG. 4, there is shown a simplified block diagram of computing device 80. Computing device 80 may include a memory 402, a processor 404, a display 406, a network interface 408, an input device 410, and/or an output module 412. Memory 402 may store application 81 and/or image data 414. Application 81 may, when executed by processor 404, cause display 406 to present user interface 416. Application 81 may also provide the interface between the tracked position of EM sensor 94 and the image and planning data developed in the pathway planning phase.

Memory 402 may include any non-transitory computer-readable storage media for storing data and/or software that is executable by processor 404 and which controls the operation of computing device 80. In an embodiment, memory 402 may include one or more solid-state storage devices such as flash memory chips. Alternatively, or in addition to the one or more solid-state storage devices, memory 402 may include one or more mass storage devices connected to the processor 404 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 404. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 80.

Network interface 408 may be configured to connect to a network such as a local area network (LAN) consisting of a wired network and/or a wireless network, a wide area network (WAN), a wireless mobile network, a Bluetooth network, and/or the internet. Input device 410 may be any device by means of which a user may interact with computing device 80, such as, for example, a mouse, keyboard, foot pedal, touch screen, and/or voice interface. Output module 412 may include any connectivity port or bus, such as, for example, parallel ports, serial ports, universal serial busses (USB), or any other similar connectivity port known to those skilled in the art.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure. While the preceding embodiments are described in terms of bronchoscopy of a patient's airways, those skilled in the art will realize that the same or similar devices, systems, and methods may be used in other lumen networks, such as, for example, the vascular, lymphatic, and/or gastrointestinal networks as well.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto as well as the ultimate use of predictive modeling to determine and update the data.

What is claimed is:

1. A method of intra-procedurally updating a navigational plan comprising:
   generating a first three-dimensional (3D) model from image data, the first 3D model depicting a luminal network;
   depicting a pathway to a location of a target in the first 3D model;
   determining a location of a tool within the luminal network;
   displaying a representation of the tool in the first 3D model at the determined location;

receiving intra-procedural cone beam computed tomography (CBCT) image data of at least a portion of the luminal network, wherein a distal portion of the tool is within CBCT image data;
  determining a location of the target in the CBCT image data;
  determining a difference in position of the location of the target in the CBCT image data and the first 3D model;
  updating at least a portion of the first 3D model with the CBCT image data to generate a second 3D model, wherein the second 3D model depicts the location of the target from the CBCT image data and the determined location of the tool within the luminal network;
  displaying the second 3D model;
  displaying an updated pathway from the location of the tool in the CBCT image data to the location of the target in the second 3D model;
  determining intra-operative reference data, wherein the intra-operative reference data is a difference in a determined position of the tool in the first 3D model and a determined position in the CBCT image data; and
  generating a predictive model based on the intra-operative reference data and reference data collected from a plurality of luminal networks, wherein the predictive model is of relative movement of organs and other structures during a respiratory cycle.

2. The method of claim 1, wherein the location of the tool within the luminal network is determined based on a signal from an electromagnetic (EM) sensor in the tool.

3. The method of claim 2, wherein the tool may be one or more of an ultrasound tool, an ablation tool, an optical instrument, a biopsy tool, or a catheter.

4. The method of claim 2, further comprising: registering the luminal network to the first 3D model by comparing detected locations of the tool with locations in the 3D model.

5. The method of claim 1, wherein the luminal network is airways of a patient's lungs.

6. The method of claim 5, wherein the predictive model is of relative movement the patient's lungs during a respiratory cycle.

7. The method of claim 6, further comprising modifying the second 3D model based on the predictive model and a given lung volume.

8. The method of claim 7, further comprising displaying the location of the tool in the modified 3D model.

9. The method of claim 1, further comprising displaying a localized portion of the second 3D model including the actual location of the tool, the actual position of the location of the target, and the updated pathway.

10. The method of claim 5, wherein the CBCT image data is acquired during a tidal breathing of a respiratory cycle.

11. The method of claim 5, wherein the CBCT image data is acquired during a breath hold.

12. The method of claim 1, further comprising tracking the location of the tool within the luminal network as the tool is navigated to the target.

13. A non-transitory computer-readable storage medium storing instructions which, when executed by a computer, cause the computer to:
  generate a first three-dimensional (3D) model from image data, the first 3D model depicting a luminal network;
  depict a pathwayto a location of a target in the first 3D model;
  determine a location of a tool within the luminal network;
  display on a user interface a representation of the tool in the first 3D model at the determined location;
  receive intra-procedural cone beam computed tomography (CBCT) image data of at least a portion of the luminal network, wherein a distal portion of the tool is within CBCT image data;
  determine a location of the target in the CBCT image data;
  determine a difference in position of the location of the target in the CBCT image data and the first 3D model;
  update at least a portion of the first 3D model with the CBCT image data to generate a second 3D model, wherein the second 3D model depicts the location of the target from the CBCT image data and the determined location of the tool within the luminal network;
  display the second 3D model in the user interface;
  display an updated pathway from the location of the tool in the CBCT image data to the location of the target in the second 3D model;
  determine intra-operative reference data, wherein the intra-operative reference data is a difference in a determined position of the tool in the first 3D model and a determined position in the CBCT image data; and
  generate a predictive model based on the intra-operative reference data and reference data collected from a plurality of luminal networks, wherein the predictive model is of relative movement of organs and other structures during a respiratory cycle.

14. The non-transitory computer-readable storage medium according to claim 13, wherein the instructions further cause the computer to:
  receive electromagnetic (EM) sensor data from an EM sensor in the tool; and
  register the luminal network to the first 3D model by comparing detected locations of the tool with locations in the 3D model.

15. The non-transitory computer-readable storage medium according to claim 13, wherein the predictive model is of relative movement of a patient's lungs during a respiratory cycle.

16. The non-transitory computer-readable storage medium according to claim 15, further comprising:
  modifying the second 3D model based on the predictive model and a given lung volume; and
  displaying the actual location of the tool in the modified second 3D model.

* * * * *